United States Patent [19]

Dennis et al.

[11] Patent Number: 5,308,766
[45] Date of Patent: May 3, 1994

[54] HYDROLYTIC ENZYME INHIBITORS/INACTIVATORS AND METHODS FOR USING SAME

[75] Inventors: Edward A. Dennis, LaJolla, Calif.; William N. Washburn, Titusville, N.J.

[73] Assignee: The Regents of the University of California, Oakland, Calif.

[21] Appl. No.: 713,116

[22] Filed: Jun. 10, 1991

Related U.S. Application Data

[63] Continuation of Ser. No. 399,799, Aug. 29, 1989, abandoned.

[30] Foreign Application Priority Data

Aug. 17, 1990 [WO] PCT Int'l Appl. .................. PCT/US90/04641

[51] Int. Cl.$^5$ .......................... C12N 9/99; C12N 9/14; C12Q 1/34
[52] U.S. Cl. ...................................... 435/184; 435/18; 435/195; 435/238; 514/120; 514/126; 534/727; 534/852; 534/861; 544/49; 544/102; 558/179; 558/180
[58] Field of Search .................. 534/727, 852, 861; 544/102, 49; 558/179, 180; 514/120, 126; 435/184, 238, 195

[56] References Cited

U.S. PATENT DOCUMENTS 4,847,376  7/1989  Neuman et al. ..................... 544/102

FOREIGN PATENT DOCUMENTS

30943/89   2/1989  Australia ............................. 544/102
10037583  10/1981  European Pat. Off. ............. 544/102
20271731   6/1988  European Pat. Off. ............. 544/102
20333167   9/1989  European Pat. Off. ............. 544/102

OTHER PUBLICATIONS

Washburn, W. N., et al. J. Am. Chem. Soc. 112:2042 (1990).
Washburn, W. N., et al. J. Biol. Chem. 266:5042 (1991).
Reynolds, L. J. et al., Assay Strategies and Methods for Phospholipases In: Methods in Enzymology, vol. 197, ed. E. A. Dennis, publ. Harcourt, Brace, Jovanovich (1991).
Gaetjens, E., et al., J. Am. Chem. Soc. 82:5328 (1960).
Chang, J., et al., Biochem. Pharmacol. 36:2429 (1987).
Reynolds, L. J., J. Am. Chem. Soc. 110:5172 (1988).
Abeles, R. H. Chemical and Engineering News 61, 48 (1983).

Primary Examiner—Floyd D. Higel
Attorney, Agent, or Firm—Walter H. Dreger; Jan P. Brunelle

[57] ABSTRACT

The present invention provides compounds that function as hydrolytic enzyme inhibitors (inactivators) and substrates. These compounds are useful in assays to detect and measure levels of hydrolytic enzyme activity and are more particularly useful in treatment regimens for various disease states and conditions implicating the underlying specific hydrolytic enzyme. Examples of hydrolytic enzymes include, but are not limited to, phospholipases, lipases, esterases, proteases, etc.

9 Claims, 7 Drawing Sheets

WHERE R¹,R² = H, alkyl
X = O, S, NH, N-alkyl

WHERE R³ = H , CN , NO

FIG. 7b

HYDROLYTIC ENZYME INHIBITORS/INACTIVATORS AND METHODS FOR USING SAME

RELATED APPLICATION

This is a continuing application under 35 U.S.C. 120/121 of application U.S. Ser. No. 07/399,799, filed Aug. 29, 1989 now abandoned.

FIELD OF THE INVENTION

The present invention in all of its aspects utilizes as a fundamental predicate a novel class of hydrolytic enzyme inhibitors (inactivators) and their use as 1) therapeutics for pathological disease states or conditions mediated by specific hydrolytic enzyme activity and as 2) enzyme substrates for assays. These inhibitors and substrates function as suicide-inhibitory bifunctionally linked substrates (SIBLINKS) and are characterized as an ensemble of three functional moieties: 1) one recognizable by (an) active site(s) of a given hydrolytic enzyme such that the enzyme functions hydrolytically when contacted with the inhibitor with attendant removal of that moiety, 2) leaving group that in one distinct, preferred embodiment is physiologically acceptable or in a second, distinct embodiment is a marker moiety, such as a chromophore, that can be detected and measured and 3) a remainder moiety linking the first and second that assumes a cyclic configuration after removal of the first and second moieties, which in the case of inhibitors (inactivators), attends its further reaction with the enzyme active site thus irreversibly inactivating or inhibiting bioactivity of the enzyme through covalent bond formation at said active site(s).

The novel hydrolytic enzyme inhibitors/inactivators and substrates of the present invention thus create means for assaying hydrolytic enzyme activity, and distinctly as a preferred embodiment, means for modulating hydrolytic enzyme activity in the control or treatment of various disease states or conditions in which such hydrolytic enzyme activity is implicated.

BACKGROUND OF THE INVENTION

Abeles, in a Special Report published in *Chemical and Engineering News* 61, 48 (1983) discussed generally a class of enzyme inactivators referred to as "suicide enzyme inactivators" or "mechanism-based inactivators". These inactivators, whether natural or man-made products, have a configuration that resembles the natural substrate of a natural enzyme, and therefore, are recognized by the active site of the enzyme. When the enzyme reacts with this recognizable configuration, the inactivator is modified chemically and thus converted into a compound that reacts with the enzyme leading to consequent enzyme inactivation, usually irreversible in nature. By acting on the suicide substrate (inactivator), the enzyme brings about its own destruction. The author postulates that development of inhibitors or inactivators of specific enzymes may be useful by playing an important role in the development of drugs that can interfere with normal enzyme activity. Where such enzymes have been identified as being implicated in a disease state, the use of such inhibitors or inactivators would be useful to modulate enzyme activity in the treatment or prevention of the given disease state in which the enzyme is implicated.

Research efforts have focused on the action or the mechanism of phospholipases, such as phospholipase $A_2$, as being involved in the regulation of many important cellular functions. See Lapetina, Chapter 21 "Phospholipase", *Annual Reports in Medicinal Chemistry* 19, 213, Academic Press Inc. (1984).

Attendant goals of research into inactivation or inhibition of phospholipase enzyme activity can be taken inter alia, from Chang et al., *Biochemical Pharmacology* 36, 2429 (1987). See also Dennis *Biotechnology* 5, 1294 (1987). These commentaries provide a review of the structure and biochemistry of certain phospholipases and direct the reader to other articles where more exhaustive treatment on this class of hydrolytic enzymes may be found. The authors express the suggestion that phospholipase activation may represent a rate-limiting step in the whole process of lipid mediator synthesis which has been found to be implicated in the existence of several disease states or conditions. Specifically, phospholipase $A_2$ ($PLA_2$) is thought to be the enzyme responsible for release of free arachidonic acid from membrane phospholipids that is believed implicated in the control of prostaglandin, leukotriene and related eicosanoid biosynthesis in inflammatory, etc. states. They add that inhibition of $PLA_2$ activity may offer an attractive therapeutic approach to the design of novel drugs for the treatment of such inflammation and other tissue injuries. The authors provide source and structure references for a large number of phospholipase $A_2$ enzymes and discuss the mechanism of the activation of these enzymes. Finally, they provide an analysis of the consequence of such enzyme activities, and therefore, provide a basis for a goal of drug design researchers to produce new classes of drug entities that may be useful in the treatment or control of various disease states or conditions by mediation at the level of phospholipase or other hydrolytic enzyme activity.

Thus, after $PLA_2$ becomes activated, it apparently mediates a variety of pathophysiological reactions probably via its products, lysophospholipids and arachidonic acid, and several potent biologically active substances such as prostaglandins, leukotrienes, etc. Also, when the phospholipid substrate contains an alkyl ether or plasmalogen function, the products of $PLA_2$ action include lysoPAF (PAF=platelet activating factor) or analogues which when acetylated produce PAF and analogues which are also potent biologically active substances. These products or co-products of $PLA_2$ activation are believed to be cytotoxic substances and have been implicated in several human inflammatory and allergic conditions. That and other data suggests that $PLA_2$ is most likely involved in inflammation and tissue injury associated with various diseases.

Increased levels of $PLA_2$ have also been found in rheumatoid arthritic conditions, psoriasis, pancreatitis and septic shock. Myocardial ischemia is also believed implicated by $PLA_2$ activation. $PLA_2$ may also be critically involved in lung pathophysiology, especially asthma.

All of this data suggests that an inhibition or inactivation of $PLA_2$ may be a promising one-step approach to interfere with the production of the products or co-products of such activation that are implicated in various disease states, thus leading to the potential alleviation of the disease process.

A rather detailed characterization of phospholipase enzymes is also supplied by Dennis, *Enzymes XVI*, 307, Academic Press Inc. (1983). This article provides characterization data for and purification of several phospholipases, the kinetics and reactions of which these phospholipases are believed responsible, biological effects and identification of sequences and conformational structure suggesting active site(s).

Phospholipase A$_2$ inhibition and modification by manoalide was the subject of U.S. Pat. Nos. 4,447,445 and 4,616,089. Manoalide is a marine natural product isolated from sponge and has been demonstrated to have anti-inflammatory activity in vivo. Research on this natural product implicated it to be acting on the level of phospholipase A$_2$, and it has been shown to be an inhibitor of both cobra and bee venom phospholipase A$_2$ (PLA$_2$). See Lombardo et al., *J. Biol. Chem.* 260, 7234 (1985) and Deems et al., *Biochem. Biophys. Acta.* 917, 258 (1987). Research on synthetic analogues extending from that is described by Reynolds et al., *J. Am. Chem. Soc.* 110, 5172 (1988). These studies show that manoalide causes a time-dependent irreversible inactivation of PLA$_2$ indicated by the modification of lysine residues. A disadvantage attending the use of manoalide is its nonspecific reactivity with a variety of proteins.

Encouraged by this goal to produce endogenous substances that could modulate hydrolytic enzyme activity, such as phospholipase, it is an object of the present invention to produce substances that can interfere with disease states or conditions via molecular interaction of specific hydrolytic enzyme activity on a suicidal inactivation or inhibitor mechanistic level. Based upon such research and study, using phospholipase A$_2$ as a model, the present research focused on the design of novel hydrolytic enzyme inhibitors (inactivators) that function via recognition by the active site of such enzymes resulting in inhibition of enzyme functionality. Thus, the inhibitors hereof invite functional suicide of the enzymatic activity.

SUMMARY OF THE INVENTION

Taken in its several aspects, the present invention stems from a fundamental predicate based upon a novel class of hydrolytic enzyme inhibitors (inactivators) as well as substrates. These novel compounds function after recognition as substrates and processing by a specific hydrolytic enzyme, inhibiting said enzyme or inactivating said enzyme irreversibly. This means forms the basis of therapeutics and of methods of treatment using such therapeutics. At the same time, a by-product of this reaction may be produced in the form of a detectable and measurable moiety that can be used as a means of measuring the amount of hydrolytic enzyme activity in a sample. This means forms the basis of an assay hereof for measuring hydrolytic enzyme activity. When used in this form, the inhibitory properties of the compounds are not necessarily clinically exploited. The present invention further produces associated means and kits, for example, germane to the assay and (clinically) distinct treatment methods defined above.

All of the foregoing aspects in all of their associated embodiments that will be represented as equivalents within the skill of the relevant art are also included within the ambit of the present invention.

The novel hydrolytic enzyme inhibitors (inactivators) and substrates of the present invention may be represented by the following generic formula (I):

(I)

wherein
- R is an oxygen atom or an imino group,
- each X independently is an oxygen atom, a sulfur atom or an imino group,
- A is an enzyme-specific moiety that facilitates recognition by and hydrolysis of the bond linking AX with C(O)Y by a target hydrolytic enzyme,
- B is a component of a physiologically acceptable leaving group BX that together with the enzyme hydrolysis of AX, attends intramolecular cyclization of the functional residue,
- Y is a linker that provides a steric environment facilitating intramolecular cyclization of said functional residue with consequent reactivity with the active site of said target hydrolytic enzyme.

In respect of use of compounds of the above formula in assays, distinct from clinical, therapeutic use, B alternatively is a marker moiety susceptible to detection and measurement upon cleavage of the bond linking BX with C(R)Y attending said intramolecular cyclization. In this case, the product of said intramolecular cyclization would not be designed to consequently react with the enzyme as this would interfere with the intended use as an assay substrate.

More specifically, the novel hydrolytic enzyme inhibitors (inactivators), and substrates, of the present invention, as represented above by Formula (I), can be represented as a preferred subgrouping of compounds of the following Formula (II):

wherein A and B are as alternatively defined above and $C_{2,3}$ represents a linker species having at least two or three carbon atoms that can be saturated or unsaturated, unsubstituted or substituted.

With respect to each class of compounds represented above by Formulas (I) and (II) for use as a therapeutic, B is physiologically acceptable, and for distinct use as a substrate in an assay, B is preferably a chromophore group, such as p-nitrophenyl.

Further preferred of the class of novel compounds hereof as represented above by Formulas (I) and (II), and as further defined above in the more particular definitions of Group B, Group A is preferably selected from a grouping that has a glycerol backbone wherein one oxygen atom is linked to the linker of the above representative compounds; other hetero atoms attached to the glycerol backbone are linked: one, either oxygen, nitrogen or sulfur, to an alkyl or a fatty acid chain, and one, an oxygen, via a phosphodiester or other suitable linkage with a polar group, for example, choline. The fatty acid chain can be a saturated or unsaturated chain that will correspond with the substrate specificity, if any, of the specific hydrolytic enzyme in question.

In addition to the mutually distinct, two-pronged aspect of the present invention represented by the novel inhibitors/inactivators versus assay substrates, in a second aspect, the present invention is directed to the method and means for treating a pathological disease state or condition mediated by a specific hydrolytic enzyme activity comprising administering to a subject susceptible to or experiencing said pathological disease state or condition an amount of novel hydrolytic enzyme inhibitor (inactivator) hereof, as represented above wherein B is physiologically acceptable, sufficient to irreversibly inactivate or inhibit said hydrolytic enzyme activity, said hydrolytic enzyme inhibitor (inactivator) being administered in a pharmaceutically acceptable form.

In another aspect, the present invention involves an assay for measuring specific hydrolytic enzyme activity in a sample, such as a biological sample taken from a human being, comprising contacting said sample with a hydrolytic enzyme substrate hereof, as represented above wherein B is a marker moiety, in a manner and under conditions such that said compound is brought into contact in situ chemically proximate to a target, specific hydrolytic enzyme, if present in said sample, so as to be reactive therewith, and measuring and detecting the amount of such activity via cleavage of and detection and measurement of a marker moiety from said compound upon reaction of said compound with said hydrolytic enzyme activity.

The present invention as defined above in its various aspects includes all associated means and methods in the form of pharmaceutical embodiments, such as formulations and methods for preparing them, pharmaceutical uses, and so forth, and in respect more specifically to assay embodiments, kits that are assembled and useful in a manner germane to the assay.

The present invention is described mechanistically in the manner it is presumed to biologically function; however, it shall be understood that the mechanism as such is not necessarily included within the ambit hereof should it actually differ in detail from that proposed. Following the presumed mechanism, "the functional residue" is That is, the method of treatment hereof (or assay) has the endpoint of inhibition and/or inactivation of enzyme activity (or marker measurement) regardless of the precise mechanism by which such endpoints are manifested in employing the compounds hereof. In assay use, consequent reactivity of the intramolecular cyclization product with the enzyme is to be avoided.

DETAILED DESCRIPTION OF THE INVENTION

All documents referred to herein are hereby expressly incorporated by reference.

The present invention is illustrated by means of a model system whereby particular novel hydrolytic enzyme inhibitors (inactivators) and substrates hereof are used in connection with phospholipase $A_2$. The approach of this invention, as illustrated herein by the model system, can be and is generalized to facilitate the development of various other specific hydrolytic enzyme inhibitors and substrates hereof, in assays or treatment regimes for other specific hydrolytic enzymes. Included among such other hydrolytic enzymes are phospholipases, lipases, esterases, proteases, etc. Therapeutic applications for inhibitors hereof for these classes of enzymes arise from conditions of inflammation, hypertension, lipid metabolism, obesity, etc. Assays based on the approach of this invention are selective, inexpensive and convenient for the important enzymes within these classes.

The essential feature of the compounds hereof is the employment of a bifunctional link to join in a molecular ensemble functionally comprising the necessary structural features required for recognition by a specific hydrolytic enzyme active site(s) and a leaving group, that in the case of therapeutic applications is physiologically acceptable, and that in the case of assay substrate applications is detectable and measurable, both incidental to the reactions of the compounds hereof with a specific hydrolytic enzyme. In preferred embodiments, the link is a dibasic acid capable of forming a cyclic anhydride. Upon enzymatic hydrolysis of the bond joining the link to the moiety conveying enzymatic specificity, the carboxylate anion of the resulting hydrolysis product is thought to act as a nucleophilic catalyst to cleave the ester bond joining the leaving group and the link, generating a cyclic anhydride. The reactivity of the anhydride with the active site of the enzyme creates a covalent bond between the two thus inactivating, or at least inhibiting, enzymatic activity. The reactivity of the anhydride is sufficiently great that if it should diffuse out of the active site of the enzyme, the overwhelming probability is that it would react with water before encountering another protein.

Thus, mechanistically, upon enzymatic hydrolysis of the bond joining the link to the ensemble conveying enzymatic specificity, the carboxylate anion of the resulting hydrolysis product is thought to act as a nucleophilic catalyst to cleave the bond joining the leaving group and the link. The net result is to generate a reactive cyclic anhydride at the catalytically active site. Acylation by the anhydride of a nucleophilic group of the enzyme irreversibly inactivates the enzyme. The rate of formation of the anhydride can be modulated by 1) adjustment of the pKa of the leaving group, and 2) introduction of alkyl or other substituents on the intervening atoms of the link, or 3) incorporation of the intervening linker atoms into a cyclic structure such as an aromatic grouping.

Figure 6A:
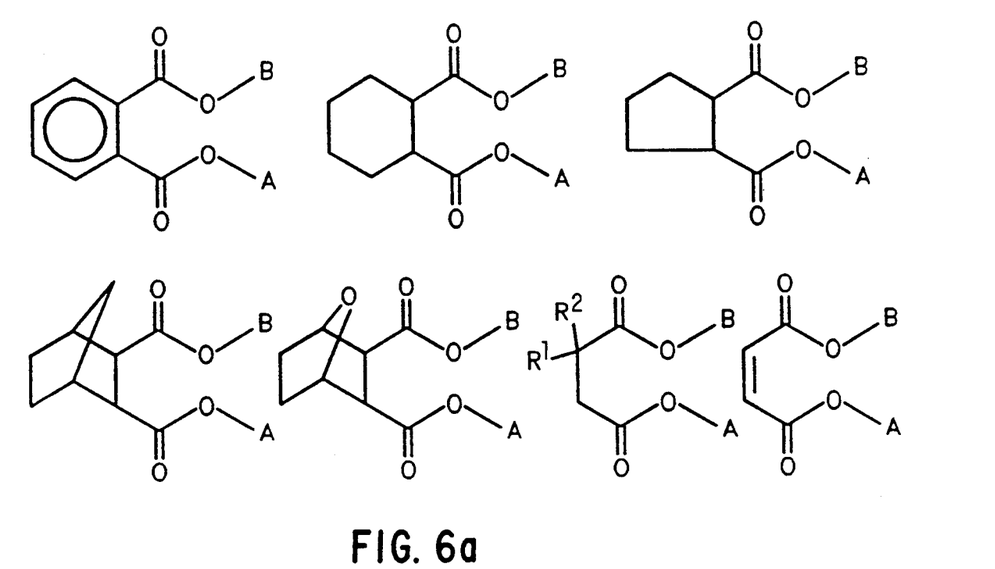
FIG. 6a depicts sample two atom linker moieties (Y) that can be employed herein.
Figure 6B:
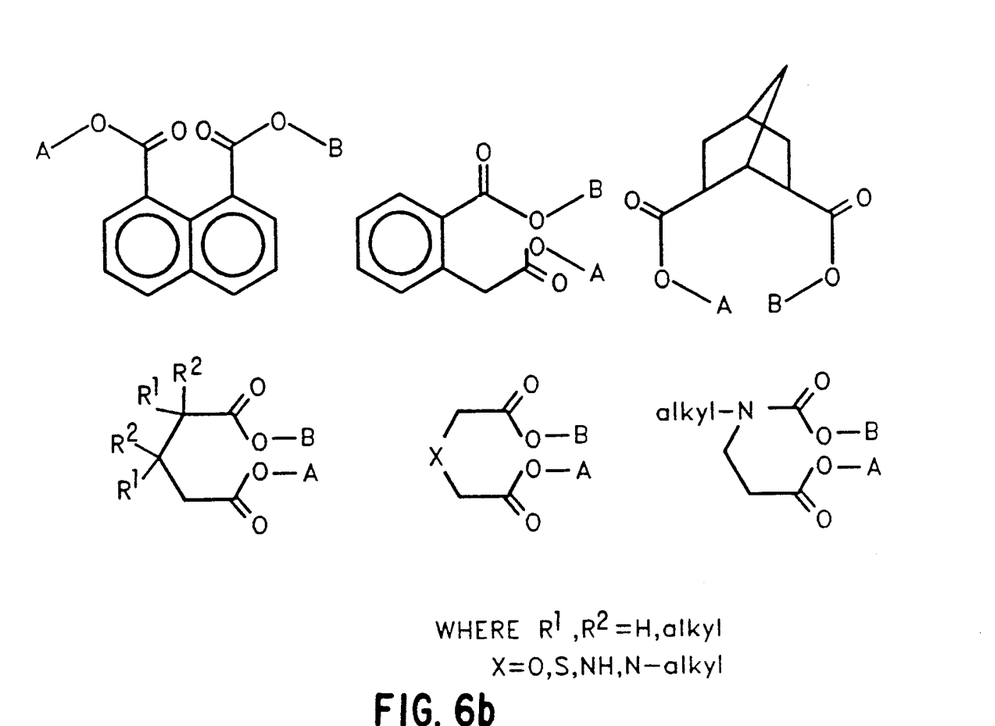
FIG. 6b depicts sample three atom linker moieties (Y) that can be employed herein.

Examples of possible two atom linker and three atom linkers depicted within complete compound structures are depicted in FIGS. 6a and 6b respectively. The starting materials bearing such linkers or for constructing such linkers are available in the art—see, e.g., the Aldrich Chemical Co. More detail concerning the chemistry is set forth infra.

The principal advantages for the novel compounds of this invention are general applicability to hydrolytic enzymes and high specificity for particular target enzymes due to 1) compound design and 2) occurrence of enzymatic acylation principally within the enzyme substrate complex that generated the cyclic compound.

The same structural features are required for this method to be used in an assay except for the requirement that moiety B be a chromophore dye or other marker and that the cyclization be sufficiently slow so that the anhydride is generated after the enzyme and the initial hydrolysis products have diffused apart.

The equivalent mechanistic principles apply where the link is a carbonyl/amide.

The chromophore or other detectable and measurable groupings are generally well known in the art. Examples of such are p-nitrophenyl, azophenyls, azonaphthyls, oxycoumarins. Examples of structures for such are given in FIG. 7b.

Figure 7A:
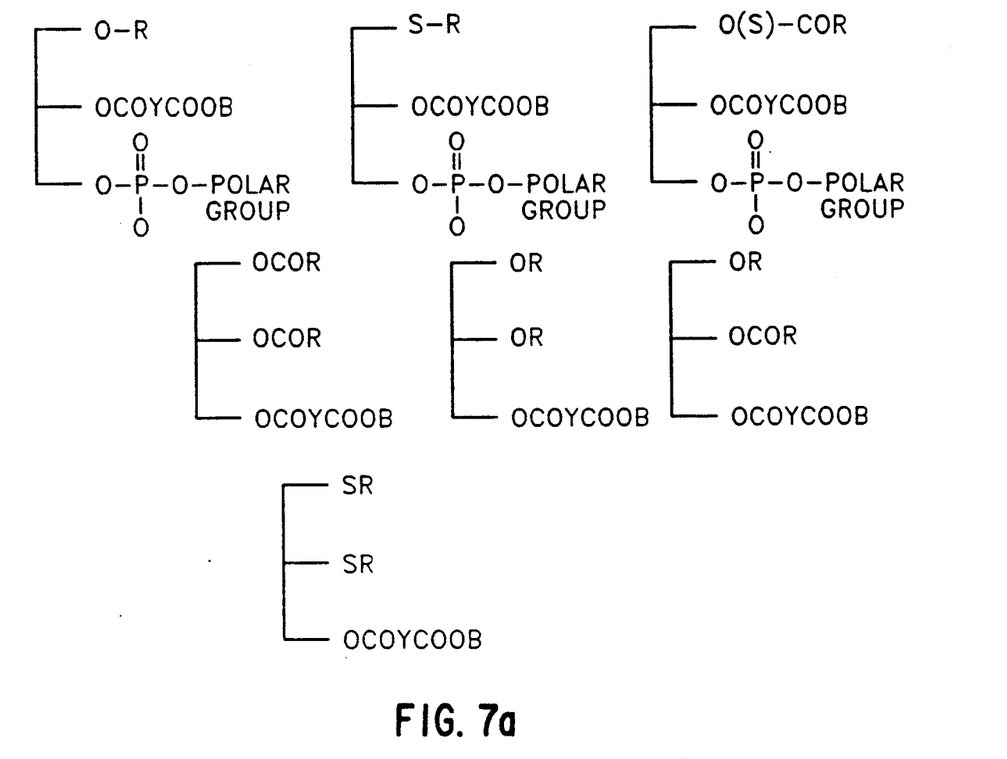
FIG. 7a depicts sample A moieties that can be employed herein.
Figure 7B:
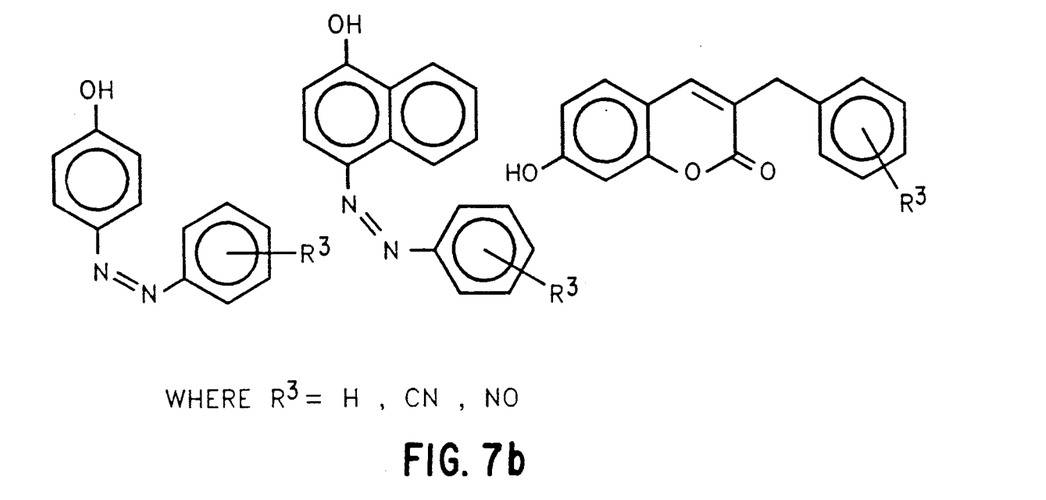
FIG. 7b depicts sample B moieties that can be employed herein.

Examples of possible structures for A (depicted with deduced linkage to the remainder of the molecule) are given in FIG. 7a. In the design of a moiety A that is specific for a given hydrolytic enzyme, advantage is taken of knowledge of the substrate specificity of the given hydrolytic enzyme. Examples of such can be taken from extant literature and include chymotrypsin, lipase, proteases and phospholipase $A_2$. More detail is provided infra.

Proteases can be subdivided into four major classes reflecting the nature of the catalytic site. Two classes promote hydrolysis of peptide bonds by nucleophilic catalysis entailing the formation of an acyl enzyme intermediate. These are the serine and cysteine proteases which utilize respectively either the hydroxyl of a serine residue or the thiol of a cysteine residue at the active site to cleave the peptide bond of the substrate. These enzymes will process nonpeptide bonds and accordingly chromogenic assays have been devised. Similarly, this substrate flexibility has allowed a variety of mechanism-based inhibitors to be developed.

The remaining two classes utilize an activated water molecule bound at the active site to cleave a peptide bond. Normally only peptide bonds are processed; consequently, chromogenic assays entailing the release of a dye as a function of enzyme activity have not been as feasible. The two classes are metallo-proteases and aspartic proteases. Good mechanism-based inhibitors for these two classes are unknown reflecting the rigorous criteria for substrate recognition.

In general, the active site of all proteases can be envisaged as lying in a cleft which may have a number of binding pockets to accommodate not only the side chain residues of the amino acid residue that comprise the peptide linkage to be cleaved but also the side chains of the amino acid residues that precede and follow the peptide bond to be cleaved. The high substrate specificity is a reflection not only of the binding requirements in the vicinity of the active site but also of these additional binding sites. Sites that bind to side chain residues that lie toward the N-terminus of the substrate are labeled $s_1$-$S_n$ proceeding away from the active site; similarly, sites that bind residues extending toward the C-terminus are labeled $s_{1'}$-$s_{n'}$. Proteases can either be exopeptidase (cleaves the first or last peptide bond of the substrate) or endopeptidases (cleaves a peptide bond embedded in the substrate).

To modulate the activity of proteases, the inhibitor must contain appropriate functionality such that "A" occupies the necessary $s_{1'}$-$s_{n'}$ recognition. "Y" and "B" would occupy the $s_1$ site. Some endopeptidases require occupancy of the $s_2$ and $s_3$ sites. In these cases the structure of "Y" must include features which would meet these requirements for substrate recognition. This is most easily accomplished by Y being a substituted aspartic or glutamic acid.

The following is a partial listing of therapeutically useful targets by enzyme class.

Metallo-proteases

1) Collagenase, arthritis
2) Elastase, emphysema, inflammation
3) Angiotensin converting enzyme, hypertension Aspartic proteases 1) HIV protease, AIDS proliferation
2) Renin, hypertension
3) pepsin, ulcer Cysteine Proteases 1) Cathepsin B, inflammation

Serine Proteases

1) Trypsin, pancreatitis
2) Granulocyte elastase, inflammation
3) Thrombin, coronary infarction

For each of the above enzymes, the design of suicide inhibitors would be guided by known substrate requirements, and secondly, if available, X-ray structural data. For example, renin recognizes the sequence HisProPheHisLeuValIleHis and cleaves the Leu-Val bond. Replacement of the Leu residue with an aspartic acid residue in which the terminal carboxyl group was esterified with a leaving group "B" would generate a substrate that upon processing would generate a cyclic anhydride which upon acylation of renin could render it inactive. See Barrett & Salvesen Ed. *Proteinase Inhibitors* Vol. 12 Elsevier, Amsterdam (1986) and *Hydrolytic Enzymes* Ed. Neuberger & Brocklehurst, Elsevier, Amsterdam (1987).

The chemistry of preparing the novel hydrolytic enzyme inhibitors (inactivators) and substrates hereof is generally known to the skilled organic chemist. For example, where one is employing a dibasic acid in preferred embodiments hereof, both moieties A and B can be attached via usual esterification reactions. The dibasic acid starting material is either known in the art or can be prepared by standard dibasic acidification procedures. See standard organic chemistry and procedure texts.

Given the modular nature of the ensemble, the synthetic sequences can be either: 1) reaction of the AXH with an activated dibasic acid followed by activation and reaction with BXH, or 2) synthesis of utilizing the procedure of Gaetjens et al., *J. Amer. Chem. Soc.* 82, 5328 (1960), for example, followed by activation and reaction with AXH.

A typical reaction pathway could include heating a mixture of a lysophospholipid, e.g., 1-decanoyl-sn-glycerol-3-phosphorylcholine with an excess of an anhydride, e.g., 2,2-dimethylglutaric anhydride in methylene dichloride in the presence of a base, e.g., triethylamine. After purification of the product half-acid phospholipid on silica gel, this product would be activated by reaction with an excess of an activator, e.g., oxalyl chloride, in methylene dichloride to produce an acid chloride. This would be subsequently reacted with an excess of the desired BXH group, e.g., p-nitrophenol, and base, e.g., triethylamine. The product in methylene dichloride would then be purified. Alternatively, the BXH group, e.g., p-nitrophenol, as an example where its cleavage could be followed spectrophotometrically, could be mixed with an equivalent of base, e.g., sodium hydroxide, and allowed to react with an equivalent of the desired anhydride, e.g., 2,2-dimethylglutaric acid to produce the half-acid. This product can in turn be activated, e.g., with oxalylchloride, and reacted with a lyso phospholipid, e.g., 1-decanoyl-sn-glycerol-3-phosphorylcholine, to produce the desired final product.

Where the novel compounds hereof are selected from those wherein R is NH and/or each X is sulfur or NH, again, standard organic chemistry reactions apply. Briefly, where R is NH, for an example, hydrogen chloride can be bubbled through a methylene chloride solution containing a equimolar mixture of 4-cyanobutyric acid and p-nitrophenol to generate the imino ether. Treatment of this compound with oxalyl chloride in Trimethylene chloride followed by removal of the oxalyl chloride under vacuum and then by addition of moiety AXH and one equivalent of base generates the desired compound.

Where either X is sulfur or nitrogen, the same procedure as described infra for the X=oxygen compounds would be followed except for the substitution of the appropriate ASH or $ANH_2$ for AOH or BSH or $BNH_2$ for BOH.

Having described the particular model system employed in the present research for providing the generic class of hydrolytic enzyme inhibitors hereof, and having supplied the methodology for preparing such based upon generally well known organic chemistry reactions, and having illustrated an assay system whereby this model system can be employed in the case of Phospholipase $A_2$, and having supplied information useful to prepare pharmaceutically acceptable compositions of such compounds for use in the treatment of implicated disease states or conditions, the present disclosure is sufficient to enable one to prepare other inhibitors (inactivators) and substrates hereof and devising assays, methods of treatment and kits, etc., for their employment in an equivalent pharmaceutically based regimen. Thus, researchers using extant literature and techniques and the present concept shall well enough know how to prepare and design inhibitors (inactivators) and substrates of the present invention for specific hydrolytic enzymes either known or yet to be discovered. Thus, one would 1) very the structural features of the natural substrate to identify the basic requirements, 2) synthesize a compound containing these features (embodied in moiety A), 3) covalently join A and Y (the link), and 4) attach B to the basic AY ensemble.

1. BRIEF DESCRIPTION OF THE DRAWINGS

FIG. 1 is a schematic representation of the mechanism whereby a number of novel hydrolytic enzyme inhibitors (inactivators) hereof function in respect to their reactivity with a hydrolytic enzyme. Depicted in detail are five (5) such novel compounds (1a-1e) hereof that are specific, via the glycerol backbone based side chain (moiety A as defined above) for phospholipase hydrolytic enzymes, depicted in FIG. 1 as $PLA_2$. They are also specific to compounds having a chromophore (p-nitrophenyl) leaving group because the inhibition-/inactivation endpoints could be facilitated in an in vitro system by the readily measurable p-nitrophenyl chromophore. The first step of the depicted reaction shows the cleavage by $pLA_2$ of the moiety A glycerol based enzyme specific side chain resulting in it being cleaved away leaving a carboxylate anion containing at the other end of the linker the para-nitrophenyl chromophore grouping. Upon a subsequent non-enzymatic catalyzed intramolecular cyclization, that chromophore grouping is cleaved away for detection and measurement, leaving a cyclized compound which serves to acylate via a nucleophilic reaction with $PLA_2$ to form the species of $PLA_2$ that is inactivated by covalent bond reaction.

2. DEFINITIONS

By the terms relating to the linker depicted above by Y in the above formulas, is meant a moiety that serves two functions: It has at each end appropriate functionality so as to be capable of linkage with moieties A and B. In further preferred embodiments, that linkage is via carboxylate functionality. The second requirement is that it contain structural, steric features that favor formation of a cyclic compound upon enzymatic cleavage of the side grouping A and concomitant expulsion of B. In further preferred embodiments, the linker would contain at least two or three carbon atoms, saturated or unsaturated, substituted or unsubstituted. It may be a part of an aromatic arrangement such as is illustrated by a phenyl or naphthalene grouping. The only limitations foreseen are that upon cleavage of side groupings A and B, in situ chemically proximate to the target enzyme, it would intramolecularly bond so as to form a cyclic compound. In the case of the preferred embodiment, the end cyclic compound would be an anhydride (see FIG. 1, for example).

By the term referring to a moiety capable of binding to an active site is meant an active site specific moiety that is recognizable by a particular hydrolytic enzyme. In the case of lipases, such a moiety could contain a glycerol backbone where one of the oxygen atoms is linked to the linker and the other two oxygens would be linked to a saturated or unsaturated acyl or alkyl chain appropriate to the enzyme in question. In the case of phospholipase hydrolytic enzymes, one of the two other oxygen atoms would be linked to a phosphodiester having a polar group, for example, choline, ethanolamine, serine, inositol, glycerol, methyl, etc. In the case of other esterases that act on lipids, such as cholesterol esterase, the moiety could contain cholesterol or a derivative.

In the case of proteases, the moiety capable of binding to an active site could be composed of an appropriate amino acid peptide, or analogue, depending on the substrate requirements of the particular enzyme. For some proteases certain substituents on the linker Y and the leaving group (BX) which may also be an amino acid, peptide or analogue thereof, are also appropriate.

Figure 1:
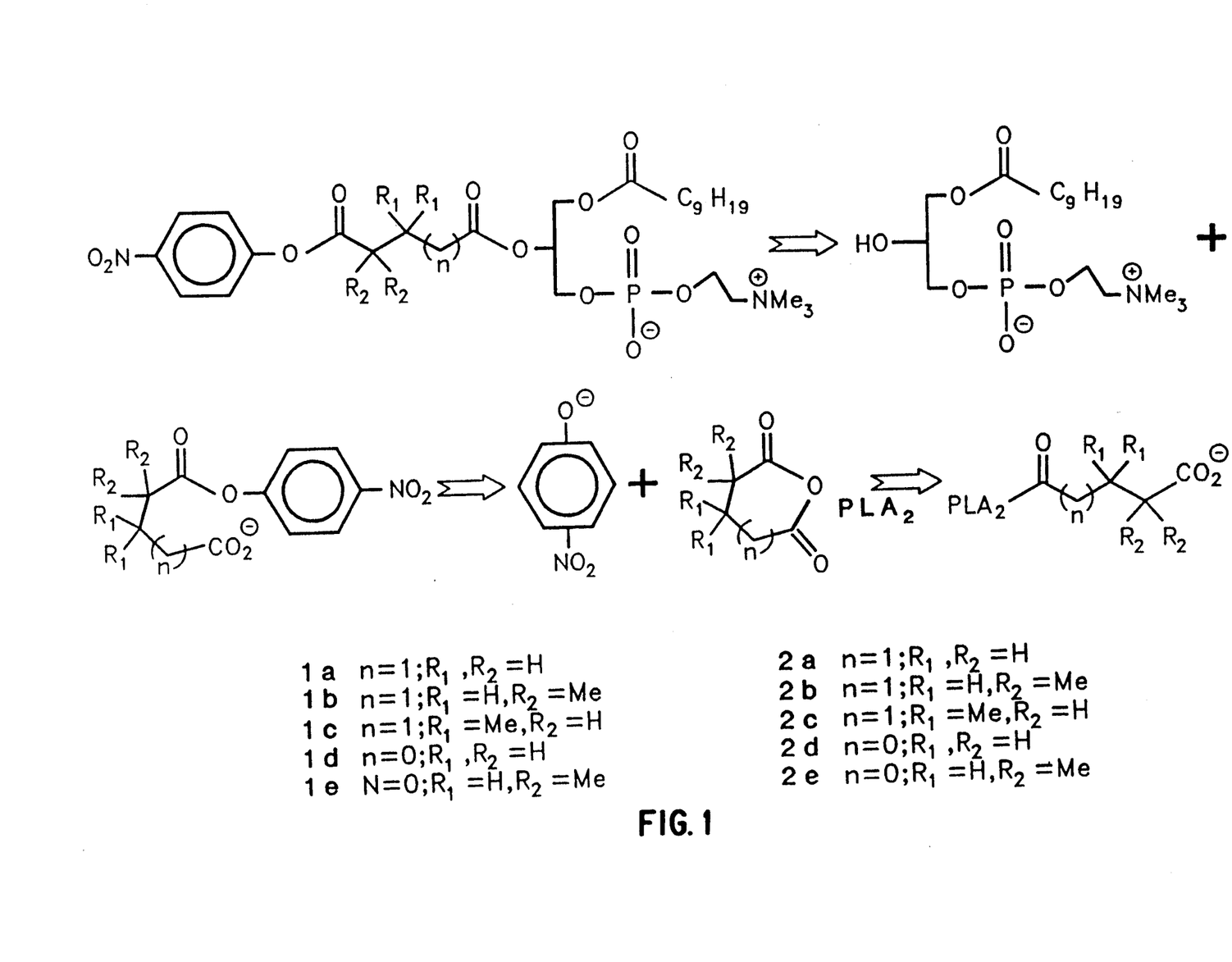

In the case of terms relating to moiety B, there are the requirements: 1) that it be a component of a good leaving group, as depicted for example in FIG. 1; 2) that, to be used in drug applications, the reaction attending intramolecular cyclization of the functional residue be generally rapid relative to diffusion and that it be a component of a physiologically acceptable leaving group; and 3) for an assay, that it be detectable and measurable.

By the term "modulating" in respect of various disease states or conditions is meant affecting the hydrolytic enzyme activity where such activity is implicated in the onset or continuance or propensity for given disease state or condition symptoms. In the case of preferred embodiments herein, various inflammatory conditions can be alleviated by use of a phospholipase $A_2$ inhibitor of the present invention so as to reduce or limit the action of said enzyme in the production of products or co-products that either themselves, or after further reactions, induce inflammatory states.

In therapeutic applications, it is essential that the compounds hereof be non-toxic or physiologically acceptable. In particular, the characterization of leaving group BX or its component B, must satisfy this criterion, as a distinct departure from its characterization when used in assay applications where it need only be detectable and measurable. Examples of physiologically acceptable leaving groups are:

(a) Substituted or unsubstituted aliphatic alcohols, thiols, or imides such as activated alcohols, e.g., trichloroethanol, trifluoroethanol, trifluoromethylmethanol.

(b) Substituted or unsubstituted cycloaliphatic or unsaturated (including aromatic) cyclic alcohols, thiols, or imides such as p-sulfophenyloxy, p-trifluoromethylphenyloxy, p-hydroxytetrafluorophenyloxy, p-halophenyloxy, o,o,p-trimethylphenyloxy, p-acetyloxyphenyloxy, p-(tritrifluoromethyl)methylphenyloxy, p-trimethylaminophnyloxy, p-cyanophenyloxy, o-carboxyphenyloxy, o-carboxy-p-aminophenyloxy, p-(N-acetylamino)phenyloxy, 2-(1-carboxyeth-1-yl)napth-6-yloxy, and so forth.

(c) Substituted or unsubstituted heterocyclic alcohols, thiols or imides such as the oxy radicals of piroxicam, diflunisal, indomethacin, tolmetin sodium, and so forth.

See also, for example, Kirby, *Adv. Phys. Org. Chem.* 17, 183–278 (1980). Physiological acceptability can be determined as well in accord with federally regulated clinical studies.

By the terms relating to detecting and measuring hydrolytic enzyme activity via a grouping suitable as such is meant any grouping that is cleavable, and detectable and measurable such as p-nitrophenol-see above. In general, one would employ spectrophotometers. However, other means of detection, such as via fluorometers or scintillation counters, may be of advantage in certain applications, particularly where greater sensitivity is required.

By "lower alkyl" or "alkyl" is meant all isomers comprising 1 to 4 carbon atoms, inclusive.

3. EXAMPLES

Preparation of Model phospholipase $A_2$ Specific Inhibitors and Substrates

Materials

All lysophospholipids, 1,2-dipalmitoyl-sn-glycero-3-phosphorylcholine (DPPC), and 1,2-dicaproyl-sn-glycero-3-phosphorylcholine (DCPC) were purchased from Avanti Polar Lipids. All cyclic anhydrides except 2,2-dimethylsuccinic anhydride were obtained from Aldrich Chemical Co. The latter was prepared by treating dimethyl-succinic acid (Aldrich) with a 3-fold excess of trifluoroacetic anhydride in $CH_2Cl_2$ for 2 hours, removing the volatiles, and using the residual solid without further purification. All solvents and reagents were of reagent quality.

$PLA_2$ obtained from cobra venom (*N. naja naja*) was purified as described in Hazlett et al., *Toxicon* 23, 457 (1985).

Preparation of Phospholipids 1a–1e

Phospholipids 1a–1e with various acyl chains in the sn-1 position, e.g., $C_qH_{1q}$, were synthesized (see FIG. 1). The general procedure employed for the synthesis of all phospholipids is described for compound 1b. To 42 mg (0.1 mmol) of 1-decanoyl-sn-glycerol-3-phosphorylcholine in 3 ml of $CH_2Cl_2$ was added 60 mg (0.43 mmol) of 2,2-dimethylglutaric anhydride followed by 50 $\mu$l (0.35 mmol) of $Et_3N$. The reaction was heated for 24 hours at 45° C. If the reaction was not complete by TLC analysis (1:10:22 $H_2O$/MeOH/$CHCl_3$ using Analtech Silica Gel G-250 glass plates with UV indicator visualized with molybdate spray), an additional 30 mg (0.21 mmol) of anhydride with 40 $\mu$l (0.28 mmol) of $Et_3N$ were added and the reaction heated for an additional 10 hours until all starting lipid was consumed. After removal of all volatile components, the residue was leached three to four times with 10-ml portions of dry $Et_2O$ to remove unreacted anhydride and triethylamine glutaric acid salts. The remaining crude half-acid phospholipid after evacuation at 0.1 torr was converted to the acid chloride upon treatment with 2 ml of $CH_2Cl_2$ containing 0.3 ml of oxalyl chloride for 5 hours at 20° C. Alternatively the half-acid phospholipid was isolated by washing with 0.1N HCl the crude acylation product dissolved in 2:1 $CHCl_3$/MeOH. Pure half-acid phospholipid was obtained after chromatography on silica gel using 1:4:30:65 HOAc/$H_2O$/MeOH/$CHCl_3$ as the eluant.

The acid chloride was separated from oxalyl chloride by removal of the volatiles in vacuo followed by two cycles of dissolution in 2 ml of dry benzene and evaporation. A solution of 60 mg (0.43 mmol) of p-nitrophenol and 60 $\mu$l (0.42 mmol) of $Et_3N$ in 4 ml of $CH_2Cl_2$ was added to a 1-ml $CH_2Cl_2$ solution of the acid chloride. If necessary, additional phenol and amine were added to ensure that an excess of p-nitrophenoxide was present. After standing overnight at 20° C., the volatiles were removed and the residue taken up in 5 ml of 2:1 $CHCl_3$/MeOH and washed with 4 ml of 0.1N HCl. The solvent was removed, and the residue containing phospholipids was chromatographed on silica gel using 10–33% MeOH/$CHCl_3$ as the eluant to give the desired phospholipid in 80–90% yield from starting material. Phospholipids 1a and particularly 1d underwent hydrolysis on silica gel, Florisil and alumina. A more satisfactory purification procedure for these two lipids entailed repeated leaching with Et$_2$O until all p-nitrophenol was removed.

Pure samples of 1a–1e were obtained after HPLC chromatography using anhydrous MeOH to elute the lipid from a Brownlee C$_{18}$ column. The p-nitrophenyl esters of SIBLINKS 1a and 1d are especially prone to hydrolysis in polar solvents such as alcohols. Storage of these compounds at $-10°$ C. in CHCl$_3$ or CH$_2$Cl$_2$ greatly enhances the stability. Therefore, HPLC-purified SIBLINKS were immediately transferred to CHCl$_3$ for storage. In an aqueous environment, the stability is enhanced when incorporated into vesicles or Triton micelles. The following are representative spectral data for lipids 1b, 1c, 1d and 1e containing a decanoyl (C$_{10}$) chain moiety at the sn-1 position.

1b: $^1$H NMR (CDCl$_3$) δ0.9 (t, 3H), 1.3 (s, 12H), 1.4 (s, 6H), 1.6 (m, 2H), 2.05 (t, 2H), 2.25 (t, 2H), 2.45 (t, 2H), 3.3 (s, 9H), 3.7 (m, 2H), 4.0 (m, 2H), 4.15 (m, 1H), 4.3 (m, 2H), 4.4 (m, 1H), 5.2 (m, 2H), 7.3 (ABq, 2H), 8.25 (ABq, 2H) MS(FAB) m/e 675.

C$_{31}$H$_{52}$N$_2$O$_{12}$P

Exact mass calculated: 675.3258

Found: 675.3267

1c: $^1$H NMR (CDCl$_3$) δ0.9 (t, 3H), 1.25 (s, 6H), 1.3 (s, 12H), 1.6 (m, 2H), 2.25 (t, 2H), 2.55 (s, 2H), 2.75 (s, 2H), 3.4 (s, 9H), 3.75 (m, 2H), 4.0 (m, 2H), 4.15 (m, 1H), 4.3 (m, 2H), 4.4 (m, 1H), 5.25 (m, 1H), 7.3 (ABq, 2H), 8.3 (ABq, 2H) MS(FAB) m/e 675.

C$_{31}$H$_{52}$N$_2$O$_{12}$P

Exact mass calculated: 675.3258

Found: 675.3245

1d: $^1$H NMR (CDCl$_3$) δ0.9 (t, 3H), 1.3 (s, 12H), 1.6 (m, 2H), 2.25 (t, 2H), 2.75 (t, 2H), 2.9 (t, 2H), 3.3 (s, 9H), 3.75 (m, 2H), 4.0 (m, 2H), 4.15 (m, 1H), 4.3 (m, 2H) 4.4 (m, 1H), 5.25 (m, 1H), 7.3 (ABq, 2H), 8.3 (ABq, 2H) MS(FAB) m/e 633.

C$_{31}$H$_{46}$N$_2$O$_{12}$P

Exact mass calculated: 633.2788

Found: 633.2800

1e: $^1$H NMR (CDCl$_3$) δ0.9 (t, 3H), 1.3 (s, 12H), 1.42 (s, 3H), 1.45 (s, 3H), 1.6 (m, 2H), 2.25 (t, 2H), 2.8 (s, 2H), 3.3 (s, 9H), 3.75 (m, 2H), 4.0 (m, 2H), 4.15 (m, 1H), 4.35 (m, 2H), 4.4 (m, 1N), 5.25 (m, 2H), 7.3 (ABq, 2H), 8.3 (ABq, 2H) MS(FAB) m/e 661.

C$_{30}$H$_{50}$N$_2$O$_{12}$P

Exact mass calculated: 661.3101

Found: 661.3079

Preincubation Conditions

Unless otherwise stated, lipids 1a–1e were purified by HPLC. SIBLINKS vesicles were prepared by sonicating 2–4 mg of phospholipid in 1 ml of 100 mM KCl using four 30-s pulses of a MSE 100-watt sonicator. The resulting solution was centrifuged (25 min. at 9,500×g, 4° C.). The vesicles after separation from the pellet were analyzed spectrophotometrically for free p-nitrophenol and p-nitrophenyl ester by measuring the OD at 400 nm at first pH 8 and then pH 12 using 1.5 and 1.8×10$^4$, respectively, as the extinction coefficient for p-nitrophenoxide. To minimize slow hydrolysis of the aryl ester, the vesicles were stored at 4° C. Further purification of the above vesicle preparation by ultracentrifugation (4 hours at 50,000×g, 4° C.) did not significantly alter inhibition time courses.

Standard preincubation conditions utilized 100 μm SIBLINKS as sonicated vesicles with PLA$_2$ in 20 mM Tris-HCl (pH 8.0), 10 mM CaCl$_2$, and 100 mM KCl at 20° C. The same conditions were used for preincubation with mixed micelles except for the presence of TRITON X-100 ®. The concentration of N. naja naja PLA$_2$ was 0.37 μM (5 μg/ml). The preincubation concentrations of the PLA$_2$s from other sources ranged from 5 to 20 μg/ml.

Residual Activity Determination

To determine the amount of residual enzyme activity remaining after preincubation, a titrametric assay was employed in which 5–20 μl of the preincubation solution was added to 1.7 ml of the substrate solution containing 10 mM CaCl$_2$ at 40° C. Thus, the preincubation mixture was diluted so activity toward residual SIBLINKS was negligible, and activity toward added substrate was maximized. PLA$_2$s obtained from N. naja naja and bee venoms were routinely assayed with 5 mM DPPC in mixed micelles with 20 mM TRITON X-100 ®. The assay utilized 50 ng of protein. Deems et al., Methods Enzymology 71, 703 (1981). Porcine pancreatic PLA$_2$ was assayed titrametrically with 100 ng of protein/assay and an egg lecithin/sodium deoxycholate mixture as substrate. Nieuwenhuizen et al., Methods Enzymology 32b, 147 (1974). C. Adamanteus and C. atrox PLA$_2$s were assayed titrametrically using 70 ng of protein/assay with the same DPPC/TRITON X-100 ® assay described above for N. naja naja except for the addition of 1 mg/ml of bovine serum albumin. Pluckthun et al., J. Biol. Chem. 260, 11099 (1985). Residual activities (percent) were calculated from the mol of base consumed titrametrically relative to a PLA$_2$ solution preincubated under the same conditions in the absence of the SIBLINKS.

SIBLINKS Inhibition

Typically, the reaction was simultaneously monitored spectrophotometrically and titrametrically during preincubation of PLA$_2$ with SIBLINKS vesicles. Continual spectral monitoring of p-nitrophenoxide release (400 nm; $\epsilon_{max} = 1.5 \times 10^4$ at pH 8) revealed the extent of hydrolysis (number of mol) of the inhibitor SIBLINKS as a function of time. The initial rates of PLA$_2$-catalyzed hydrolysis of SIBLINKS were based on the p-nitrophenoxide produced during the first 1% or less of the reaction, assuming instantaneous cyclization, an assumption that is not valid for substrate 1a. Titrametric assays, as described above, revealed the amount of residual enzymatic activity from which the number of mol of PLA$_2$ inactivated could be calculated. To ascertain maximum inhibition, preincubations were continued for 24 hours or less if no further loss of activity with time occurred within experimental error. The partition ratio (P) of the number of mol of SIBLINKS hydrolyzed per mol of enzyme inactivated was calculated using the above independent determinations of mol of p-nitrophenol released and mol of PLA$_2$ inactivated. P values were calculated several times during the time course of inactivation studies. P was essentially constant between 20 and 70% inactivation. The value of P for a specific SIBLINKS is an average of the three or four values measured during the determination of each inactivation time course.

Cyclic Anhydride Inhibition

The following procedure was utilized to measure PLA$_2$ inhibition by cyclic anhydrides. A CH$_2$Cl$_2$ solution of the anhydride was evaporated under an N$_2$ stream. Immediately, 400 μl of the appropriate PLA$_2$ in 20 mM Tris-HCl (pH 8.0), 10 mM CaCl$_2$, and 100 mM KCl at 20° C. was added followed by vortexing to ensure rapid mixing. Aliquots were assayed titrametrically after 5 min; no further change in activity was observed after an additional 1-2 hours.

Preparative Scale Inhibition of PLA$_2$

When large amounts of PLA$_2$ inhibited by cyclic anhydride were needed, the following procedure was employed. To 0.5-0.9 ml of buffer (0.7 M Tris-HCl, pH 8.0) containing 0.15-0.2 mg of PLA$_2$ was added 6.5-9 mg of cyclic anhydride 26. After vortexing and standing for 1 hour, a second portion of anhydride was added to ensure that maximum inhibition was obtained. The suspension was applied to a Pharmacia LKB Biotechnology Inc. G-25 PD-10 column that was preequilibrated with buffer (10 mM K$_2$HPO$^1$, pH 8), and the protein was eluted with the same buffer. Similar conditions were employed to obtain PLA$_2$ inhibited by SIBLINKS except for a 20 hour preincubation with 500 μM SIBLINKS vesicles and the inclusion of 10 mM CaCl$_2$ and 100 mM NaCl. The 0.5 ml chromatographic fractions were analyzed for protein and p-nitrophenyl ester; only protein fractions free of the SIBLINKS were utilized.

Hydroxylamine Studies

The following procedure was employed for hydroxylamine treatment. The appropriate amount of a freshly prepared stock solution of 50 mM NH$_2$OH HCl in 1M Tris-HCl (pH 8.0) was added to the PLA$_2$ solution to a final concentration of 5 mM. After vortexing and before assaying titrametrically for PLA$_2$ activity, the solution was allowed to stand 1-2 hours at 20° C. This reaction was performed in a closed vial to minimize NH$_2$OH oxidation.

Compound 1a (see FIG. 1) was prepared by acylating commercially available 1-decanoyl-2-lysophosphatidylcholine with excess glutaric anhydride and triethylamine in methylene dichloride at 40° C. After purification on silica gel using 1:4:30:65 acetic acid:water:methyl alcohol:trichloromethane, the product half acid was converted to compound 1a by sequential treatment in methylene chloride at 20° C. with 1) an excess of oxalyl chloride, 2) removal of the volatile components under vacuum in methylene chloride and 3) excess p-nitrophenol/triethylamine. Compound 1a was purified by two selective precipitations induced by dilution of a concentrated methylene chloride solution 50-fold with diethyl ether. To remove the last vestiges of p-nitrophenol, one equivalent of triethylamine was added to the methylene chloride solution to disrupt the hydrogen bonding of the phenol to the phospholipid. Hydrolysis of compound 1a appears to be catalyzed on silica gel, Florisil and alumina. Preparative HPLC using a C18 column with methanol as eluant yields 1a free of trace contaminants.

The NMR and high resolution spectra were in accord with compound 1a structurally:

$^1$H NMR (CDCl$_3$) δ0.86 (t, 3H), 1.29 (S, 12H), 1.6 (m, 2H), 2.05 (t, 2H), 2.28 (m, 2H), 2.5 (m, 2H), 2.7 (m, 2H), 3.35 (s, 9H), 3.72 (m, 2H), 3.95 (m, 2H), 4.15 (m, 1H), 4.3 (m, 2H), 4.4 (m, 1H), 5.2 (m, 1H), 7.3 (ABq, 2H), 8.25 (ABq, 2H) MS (FAB) m/e 647 Exact Mass Calc. for C$_{29}$H$_{48}$N$_2$O$_{12}$P 647.2945; found 647.2952. Other compounds falling within the scope of the present invention are prepared following analogous procedures with appropriate starting compounds as set forth in the following Table:

TABLE I

| For B Moiety | For Y Moiety | For A Moiety |
|---|---|---|
| salicyclic acid | glutaric anhydride | 1-decanoyl-lyso-PC* |
| salicyclic acid | glutaric anhydride | 1-decanoyl-lyso PE (phosphatidylethanolamine) |
| salicyclic acid | glutaric anhydride | 1-decanoyl-lyso PG (phosphatidylglycerol) |
| salicyclic acid | glutaric anhydride | 1-decanoyl-lyso PS (phosphatidylserine) |
| azonaphthol | glutaric anhydride | 1-decanoyl-lyso PC |
| azonaphthol | succinic anhydride | 1-decanoyl-lyso PE |
| azonaphthol | succinic anhydride | 1-decanoyl-lyso PG |
| azophenyl | adipic anhydride | 1-decanoyl-lyso PS |
| p-(N-acetylamino)phenol | pimelic anhydride | 1-decanoyl-lyso PC |
| p-(N-acetylamino)phenol | pimelic anhydride | 1-decanylthio-lyso PC |
| p-(N-acetylamino)phenol | 2-methylsuccinic anhydride | 1-decanylthio-lyso PG |
| p-(N-acetylamino)phenol | 2,2-dimethylsuccinic anhydride | 1-decanylthio-lyso PE |
| p-(N-acetylamino)phenyl | 1,2-dimethylsuccinic anhydride | 1-decanylthio-lyso PS |
| p-(N-acetylamino)phenol | 3,3-dimethylsuccinic anhydride | 1-decanylamino-lyso PC |
| p-trifluoromethyl phenol | maleic anhydride | 1-decanoyl-lyso-PC |
| p-trifluoro-methyl phenol | norbornyl anhydride | 1-decanoyl-lyso-PC |
| p-bromo phenyl | norbornyl anhydride | 1-decanoyl-lyso-PC |
| p-acetyloxy phenol | glutaric anhydride | 1-decanoyl-lyso-PC |
| 2-(6-hydroxynaph-2-yl)propionic acid | glutaric anhydride | 1-decanoyl-lyso-PC |
| indomethacin | naphthylene-2,8-dicarboxylic acid anhydride | 1-decanoyl-lyso-PS |
| tolmetinsodium | benzene-1,2-dicarboxylic acid anhydride | 1-hexanoyl-lyso PC |
| salicylic acid | benzene-1,2-dicarboylic acid anhydride | 1-hexanoyl-lyso PC |

*1-decanoyl-2-lysophosphatidylcholine(full name 1-decanoyl-sn-glycero-3-phosphorylcholine)

Preparation of Physiologically Acceptable SIBLINKS

To 42 mg (0.1 mmol) of 1-decanoyl-sn-glycerol-3-phosphorylcholine in 3 ml of CH$_2$Cl$_2$ is added 60 mg (0.43 mmol) of 2,2-dimethylglutaric anhydride followed by 50 μl (0.35 mmol) of Et$_3$N. The reaction is heated for 24 hours at 45° C. If the reaction is not complete by TLC analysis (1:10:22 H$_2$O/MeOH/CHCl$_3$ using Analtech Silica Gel G-250 glass plates with UV indicator visualized with molybdate spray), an additional 30 mg. (0.21 mmol) of anhydride with 40 μl (0.28 mmol) of Et$_3$N are added and the reaction heated for an additional 10 hours until all starting lipid is consumed. After removal of all volatile components, the residue is leached three to four times with 10-ml portions of dry Et$_2$O to remove unreacted anhydride and triethylamine glutaric acid salts. The remaining crude half-acid phospholipid after evacuation 0.1 torr is converted to the acid chloride upon treatment with 2 ml of CH$_2$Cl$_2$ containing 0.3 ml of oxalyl chloride for 5 hours at 20° C. Alternatively the half-acid phospholipid is isolated by washing with 0.1N HCl the crude acylation product dissolved in 2:1 CHCl$_3$/MeOH. Pure half-acid phospholipid is obtained after chromatography on silica gel using 1:4:30:65 HOAc/H₂O/MeOH/CHCl₃ as the eluant.

The acid chloride is separated from oxalyl chloride by removal of the volatiles in vacuo followed by two cycles of dissolution in 2 ml of dry benzene and evaporation. A solution of 65 mg (0.43 mmol) of p-(N-acetylamino)-phenol and 60 μl (0.43 mmol) of Et₃N in 4 ml of CH₂Cl₂ is added to a 1-ml CH₂Cl₂ solution of the acid chloride. If necessary, additional phenol and amine are added to ensure that an excess of p-(N-acetylamino)-phenoxide is present. After standing overnight at 20° C., the volatiles are removed and the residue taken up in 5 ml of 2:1 CHCl₃/MeOH and washed with 4 ml of 0.1N HCl. The solvent is removed, and the residue containing phospholipids is chromatographed on silica gel using 10–33% MeOH/CHCl₃ as the eluant to give the desired phospholipid.

Pure samples are obtained after HPLC chromatography using anhydrous MeOH to elute the lipid from a Brownlee C₁₈ column.

In accord with the foregoing procedure for the preparation of physiologically acceptable compounds hereof, useful distinctly as a drug entity, the foregoing enumerated physiologically acceptable B moieties are analogously substituted to afford the corresponding product, that is, o-(carboxyphenyloxy) and so forth.

Assays

All assays with compound 1a were measured in 0.4 ml buffer (10 mM Tris-HCl, pH8, 10 mM CaCl2, and 100 mM KCl).

Figure 2:
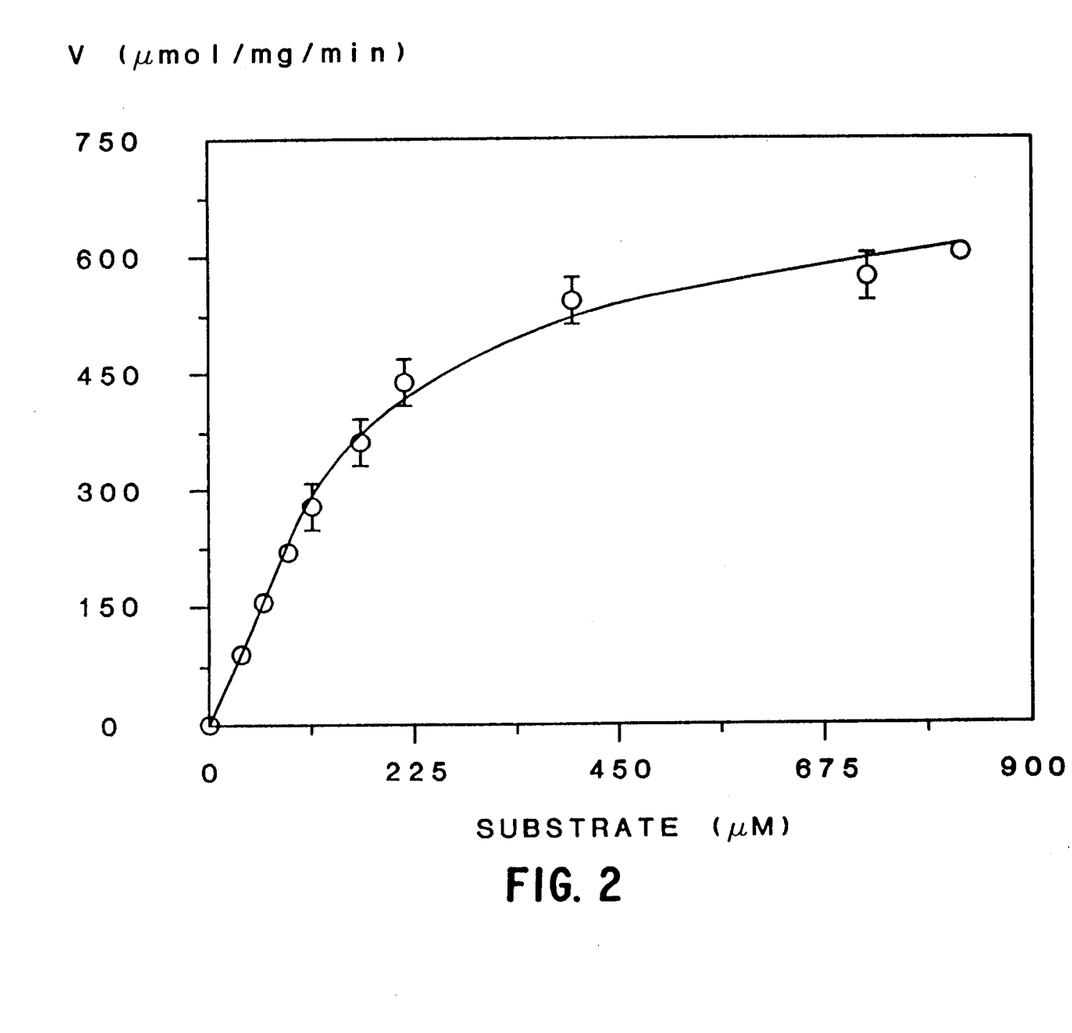
FIG. 2 contains a plot of specific activity for phospholipase $A_2$ obtained from cobra venom (Naja naja naja) as a function of the concentration of compound 1a (see FIG. 1) in 3.2:1 mixed micelles of isooctylphen(polyoxy)$_n$ol [n=average about 9.5] (TRITON X-100®) and phospholipid at 40° C.

FIG. 2 contains a plot of the specific activity for 20 ng phospholipase A₂ obtained from cobra venom (Naja naja naja) as a function of the concentration of compound 1a in 3.2:1 mixed micelles of Triton X-I00 and phospholipid at 40° C. See Dennis, *J. Lipid Research* 14, 152 (1973) and Deems and Dennis, *Methods in Enzymology* 71, 703 (1981). In 4:1 Triton/phospholipid mixed micelles, the relative V's for compound 1a and 1,2-dipalmitoyl phosphatidylcholine (DPPC) using a titrametric assay at 5 mM substrate were 1:3. The p-nitrophenol ester moiety promotes enhanced binding to hydrophobic residues in the vicinity of the active site of PLA₂ resulting in a lower concentration of substrate being required to reach half saturation for compound 1a than for DPPC.

Figure 3:
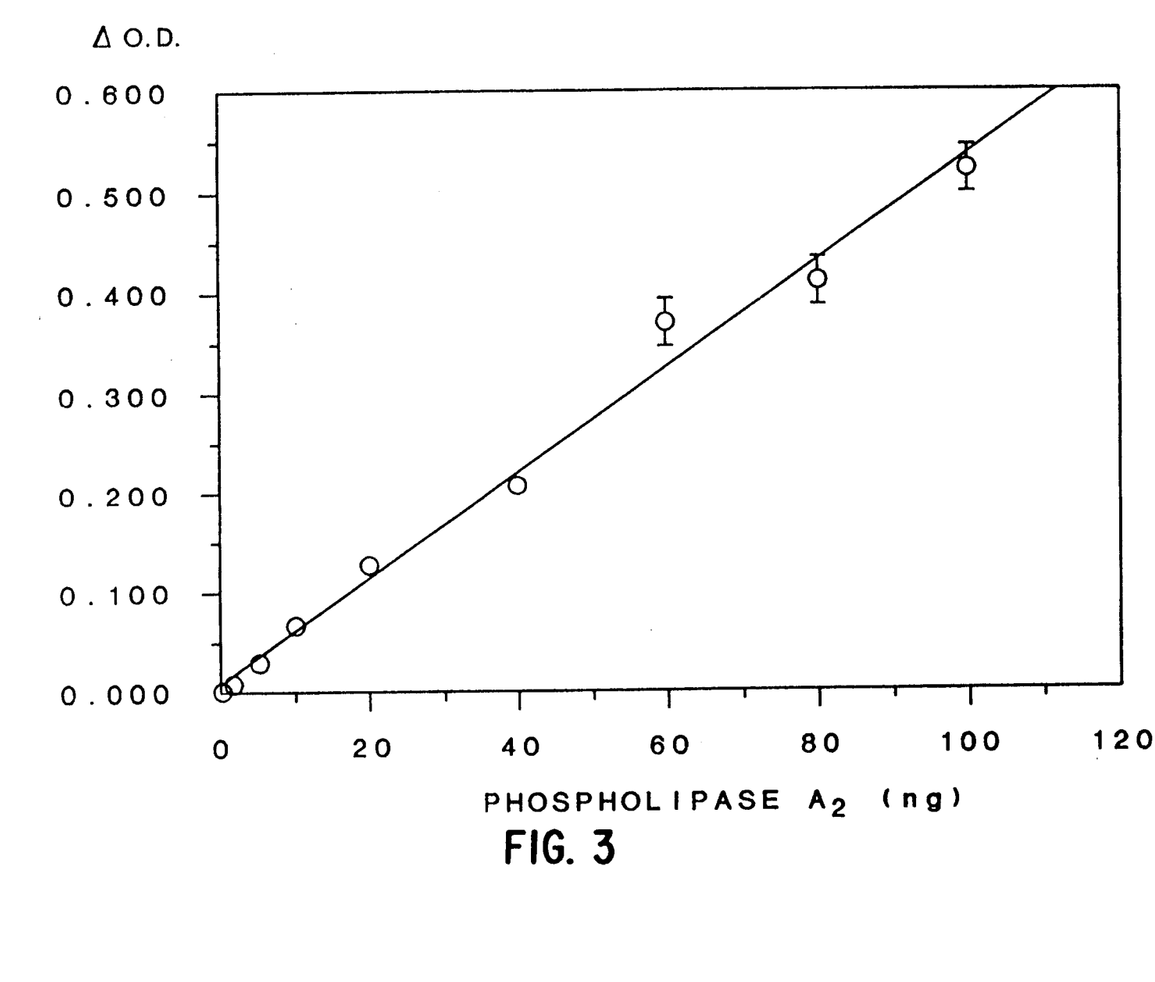
FIG. 3 shows the velocity for the hydrolysis (Δ O.D. λ 400 in 20 sec.) of 0.4 mM compound 1a in 1.8:1 TRITON X-100®: phospholipid mixed micelles at 40° C. as a function of the amount of $PLA_2$ (see FIG. 1).

FIG. 3 contains a plot of the initial velocities (expressed at Δ O.D. at λ=400 nm in 20 sec.) observed with phospholipase A₂ (specific activity 1470 Mmol min⁻¹mg⁻¹ which was linear with protein concentration from 0.5 ng to 100 ng using 1.8:1 using Triton/phospholipid mixed micelles at 40° C. containing 0.4 mM compound 1a.

The hydrolysis reaction rate is a function of the ratio of mole fraction of substrate in the Triton/phospholipid mixed micelle; the rate diminishes three-fold as the surface ratio increases from 1.6:1 to 3:1 to 4.5:1 to 7:1. Unilamellar vesicles (SUVs) prepared by sonication of compound 1a followed by centrifugation, were readily hydrolyzed by phospholipase A₂; for a 400 μM solution of SUV's, V was 265 μmol/min/mg as compared to 550 measured for 400 μM of compound 1a in 3.2:1 Triton mixed micelles.

Figure 4:
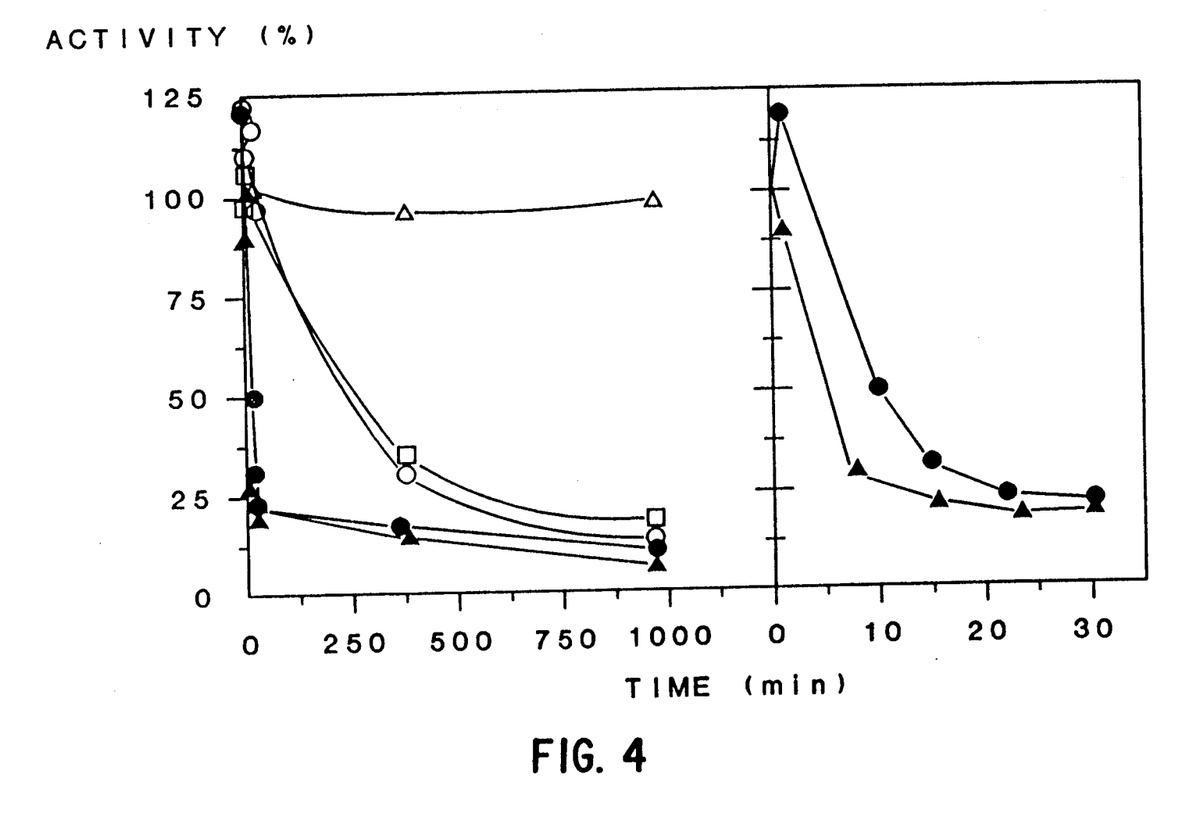
FIG. 4 shows time courses for inactivation of phospholipase $A_2$ obtained from cobra venom by preincubation of compounds 1a to 1e (see FIG. 1).

The time courses for inactivation of phospholipase A₂ obtained from cobra venom by preincubation of compounds 1a (open triangle), 1b (closed circle), 1c (open square), 1d (closed triangle), and 1e (open circle) are shown in FIG. 4. The conditions were 1) preincubate a 260:1 mixture of inhibitor 1 to PLA₂ in 1 ml solution containing 5 μg/ml of PLA₂, 100 μM vesicles of compound 1a-1e, 20 mM Tris-HCl, pH 8, 10 mM CaCl2 and 0.1M KCl at 20° C., 2) measure titrametrically the hydrolysis rate initiated by addition of a 20 μl aliquot of the above solution to 1.7 ml of 40° C. assay medium containing 5 mM 1,2-dipalmitoyl phosphatidylcholine, 10 mM CaCl2 and 20 mM Triton X-100.

TABLE II

EFFICIENCY OF HYDROLYSIS AND INHIBITION

| Substrate | V (μmol min⁻¹ mg⁻¹) | $P^a$ | Release Fragment | $t_{\frac{1}{2}}$ Cyclization (sec) |
|---|---|---|---|---|
| 1a | 155 | | 2a | 150 |
| 1b | 0.11 | 19 | 2b | 40 |
| 1c | 0.002 | 9 | 2c | 15 |
| 1d | 0.6 | 35 | 2d | 4 |
| 1e | 0.005 | 11 | 2e | 1 |

$^a$partition ratio (P) expressed as moles of dye released/mole of enzyme inactivated.

Table II contains the initial velocity constants for release of p-nitrophenol (ArOH) from substrates 1a–1e during the first 5% of the hydrolysis. Table II also contains the cyclization rates for the five release fragments 2a–2e. It is apparent that succinate derivatives are poorer substrates than their glutamate counterparts either due to the inductive effect of the ester being closer to the sn-2 ester linkage or due to steric effects of the carbonyl oxygen in what would be the position of a fatty acid. Geminal methyls in either the β or γ position retard the hydrolysis rate; however the effect is 50 fold greater for the β position.

The efficiency of enzymatic deactivation can be expressed as the partition ratio (P) as shown in Table II. From this analysis, the dimethylglutarates 1b and 1c and the dimethylsuccinate 1e are more efficient suicide inhibitors. Presumably, geminal methyl groups promote more efficient binding of 2 to the enzyme. On average, the enzyme processes 10–30 substrates before being deactivated. Inhibitor 1d is less efficient, but is processed faster. The extent of inhibition is a function of the preincubation conditions, i.e. temperature and substrate physical state (micelles vs vesicles).

Conditions which favor association of the release fragment with PLA₂ lower the P. For 100 μM 1d in 8.2:1 Triton/phospholipid mixed micelles, P increased to ~250 from ~35 for vesicles reflecting the greater propensity for 2d to be extracted away from the enzyme. Raising the temperature from 20° C. to 40° C. during the preincubation of PLA₂ with 1b or 1d had little effect on the time course, but did increase P. Presumably, micelles and higher temperatures favor diffusion of the hydrolysis products 2 away from the enzyme thereby resulting in the cyclic anhydride being generated in bulk solution and reacting with H₂O. The overall rate of inactivation is a reflection of not only the rate of intramolecular cyclization and susceptibility to enzymatic hydrolysis but also the rate of diffusion of 2 from the enzyme.

Figure 5:
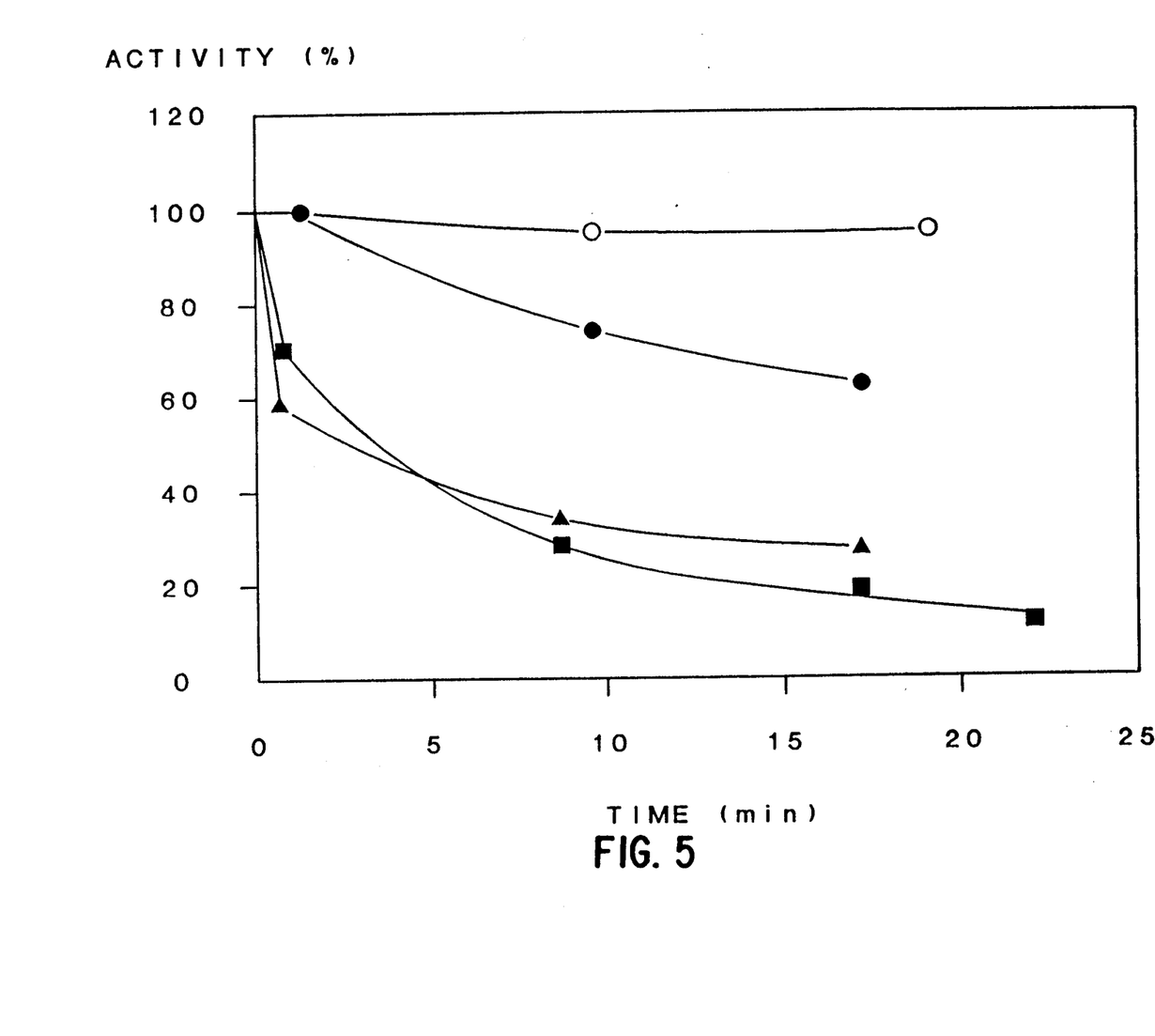
FIG. 5 shows the effect of inhibitor concentration on phospholipase $A_2$ activity for compound 1d (see FIG. 1).

The effect of inhibitor concentration is shown in FIG. 5 for 1d. Inhibition of a 70 nM solution of PLA₂ is quite rapid even at 20 mM (closed square), 5 mM (closed triangle), and 1.7 μM (closed circle) inhibitor. At concentrations of 1d of 0.5 μM (open circle) or less, 1d was consumed before the PLA₂ was inactivated. Inhibition can be observed even at lower concentrations provided the ratio of inhibitor/PLA₂ exceeds ~40 indicating that K for these inhibitors is very low. In contrast 8.2:1 Triton/phospholipid mixed micelles of 1d do not inhibit below 20 NM. Decreasing the surface concentration of the inhibitor decreases the rate of inhibition.

The reader is also directed to literature extant that supply relevant details as to specific, alternative assays in measuring activity herein, and to devising pharmaceutically acceptable compositions and methodology for the efficacious treatment of disease states, having supplied herein the essence of the present invention for essentially participating in such clinical endeavors. For example, see U.S. Pat. Nos. 4,826,958, 4,833,152, 4,616,089, 4,788,304, 4,447,445, and WO86/06100 (Oct. 23, 1986).

Drug entities prepared as described above for specific target hydrolytic enzyme inhibition and/or inactivation are compounded in accord with known techniques to produce useful pharmaceutical compositions that are pharmaceutically acceptable for appropriate administration in the treatment of pathological conditions or disease states manifested etiologically by such hydrolytic enzyme activity.

Such drugs are tested for safety, dose response and efficacy in humans as per federal regulations. Ordinary studies conducted pursuant to those regulations shall determine the safety and efficacious dose regimens appropriate in the circumstances for the treatment of the particular disease state of concern. The attendant clinical studies are in the area of routine experimentation generally within the ken of the art-skilled. These drugs are administered via standard formulations to patients with such disease states, again either topically, orally, parenterally, rectally, alone or in combination, at regular intervals or as a single bolus, or as a continuous infusion, and so forth.

For example, a typical pharmaceutical composition containing the active compound hereof together with an appropriate pharmaceutically acceptable carrier entity(ies) may be in the range of about 0.1 mg to about 500 mg per dose, or about 1 microgram to about 7 mg per kilogram of body weight. Such amount would be considered "an amount sufficient to inactivate or inhibit the activity of a given hydrolytic enzyme". Again, the end-point of such administration would be the inhibition or inactivation of the given hydrolytic enzyme manifested by an alleviation of the symptoms associated with the disease. The regulatory protocols necessary to produce marketable drug entities provide the exact dosage and the details of the "pharmaceutically acceptable form" of a compound of this invention.

The above details would, of course, not be necessary to follow in application of certain compounds of the present invention distinctly as assay substrates. As these assays would more likely be conducted in an in vitro environment, also within the ken of the art-skilled, the special precautions required for administration of drug entities to humans need not necessarily be followed.

The information contained in the part hereof supra entitled "Assays" are materials and methods and results of in vitro studies using certain of the compounds hereof as models for the testing of inhibition and/or inactivation of a particular model hydrolytic enzyme. These protocols and results are believed to be translatable within the routine experiment of the art-skilled to related enzymes of human origin, and into an animal, and hence, a human being. As mentioned above, confirmation of such translation into these in vivo systems would be readily measurable by the end point of the mechanism believed operative for the compounds of the present invention that are physiologically acceptable. Thus, in such an in vivo system, if the organism exhibits alleviation of symptoms associated with a given disease state that is known to be linked to a particular hydrolytic enzyme against which the test compound hereof is effected, then activity in such a biosystem with such test compound can be presumed in line with and consequential to the corresponding in vitro tests, as provided above.

The foregoing description details specific methods that can be employed to practice the present invention. Having detailed specific methods initially used to characterize, prepare and use the inhibitors (inactivators) and substrates hereof, and further disclosure as to specific model systems, those skilled in the art will well enough know how to devise alternative reliable methods for arriving at the same information and for extending this information to other hydrolytic enzyme systems. Thus, however detailed the foregoing may appear in text, it should not be construed as limiting the overall scope hereof; rather, the ambit of the present invention is to be governed only by the lawful construction of the appended claims.

What is claimed is:

1. A method of inactivating or inhibiting a phospholipase A enzyme, comprising administering to a subject susceptible to or experiencing a condition mediated by the activity of said enzyme an amount sufficient to inactivate or inhibit the activity of said enzyme of a pharmaceutically acceptable form of a compound of the formula:

wherein
R is oxygen or imino,
each X independently is oxygen, sulfur or imino,
A is a moiety recognized by phospholipase A enzyme such that said enzyme hydrolyses the bond linking AX with C(O)Y,
B is a physiologically acceptable leaving group,
Y is an alkylene or alkenylene or alkylene or alkenylene substituted with one or more lower alkyl groups.

2. The method according to claim 1 wherein, in said compound, AX is 1-decanoyl-sn-glycero-3-phosphorylcholine.

3. The method according to claim 2 wherein, in said compound, Y is n-propylene.

4. The method according to claim 2 wherein, in said compound, Y is 1,1-dimethyl-n-propylene.

5. The method according to claim 2 wherein, in said compound, Y is 2,2-dimethyl-n-propylene.

6. The method according to claim 2 wherein, in said compound, Y is ethylene.

7. The method according to claim 2 wherein, in said compound, Y is 1,1-dimethylethylene.

8. The method according to claim 2 wherein, in said compound, XB is trihaloethyloxy.

9. The method according to claim 8 wherein, in said compound, XB is trifluoroethyloxy.

* * * * *

UNITED STATES PATENT AND TRADEMARK OFFICE
CERTIFICATE OF CORRECTION

PATENT NO. : 5,308,766
DATED : May 3, 1994
INVENTOR(S) : EDWARD A. DENNIS, et al.

It is certified that error appears in the above-indentified patent and that said Letters Patent is hereby corrected as shown below:

In Col 7, line 38, delete "$s_1$-$S_n$" and insert therefor --$s_1$-$s_n$--.

In Col. 10, lines 6 and 7, delete "isooctylphen(-polyoxy)$_n$ol" and insert therefor --isooctylphen(polyoxy)$_n$ol--.

In Col. 16, in TABLE 1, in all occurrences, change the spelling of "salicyclic" to --salicylic--.

In Col. 16, in TABLE 1, in all occurrences, change the spelling of "p-bromo phenyl" to --p-bromo phenol--.

Signed and Sealed this

Twentieth Day of September, 1994

Attest:

BRUCE LEHMAN

*Attesting Officer*  *Commissioner of Patents and Trademarks*